(12) United States Patent
Kokeguchi et al.

(10) Patent No.: US 8,562,957 B2
(45) Date of Patent: Oct. 22, 2013

(54) OILY HAIR COSMETICS

(75) Inventors: Yuki Kokeguchi, Narita (JP); Kyoichi Takeda, Narita (JP); Kiyotaka Kawai, Narita (JP)

(73) Assignee: Kokyu Alcohol Kogyo Co., Ltd., Narita-Shi (JP)

( * ) Notice: Subject to any disclaimer, the term of this patent is extended or adjusted under 35 U.S.C. 154(b) by 515 days.

(21) Appl. No.: 12/697,182

(22) Filed: Jan. 29, 2010

(65) Prior Publication Data

US 2010/0203003 A1    Aug. 12, 2010

Related U.S. Application Data

(60) Provisional application No. 61/148,918, filed on Jan. 30, 2009.

(51) Int. Cl.
A61K 8/00 (2006.01)
A61K 8/39 (2006.01)
A61Q 5/12 (2006.01)

(52) U.S. Cl.
CPC .... *A61K 8/39* (2013.01); *A61Q 5/12* (2013.01)
USPC ...................................................... 424/70.1

(58) Field of Classification Search
None
See application file for complete search history.

(56) References Cited

FOREIGN PATENT DOCUMENTS

| JP | A1988183517 | 7/1988 |
| JP | 1993-163120 A | 6/1993 |
| JP | 2001-226235 A | 8/2001 |
| JP | 2001-342116 | * 12/2001 |
| JP | 2002-47122 | * 2/2002 |
| JP | A2004143098 | 5/2004 |
| JP | A2005206467 | 8/2005 |
| JP | 2008-127342 A | 6/2008 |
| JP | 2008-137916 A | 6/2008 |
| JP | 2008-174496 A | 7/2008 |
| JP | 2008-273902 A | 11/2008 |
| JP | A2009035497 | 2/2009 |
| WO | WO-2008-096845 A1 | 8/2008 |

OTHER PUBLICATIONS

Japan Patent Office, PCT/JP2009/051614 International Search Report, May 12, 2009, pp. 1-13.

* cited by examiner

*Primary Examiner* — Brian Gulledge
(74) *Attorney, Agent, or Firm* — The Harris Firm

(57) ABSTRACT

Conventional hair cosmetic materials have difficulty in achieving both high improvement effects on damaged hair and excellent sensation upon use. The present invention provides an oil-based hair cosmetic material to realize hair cosmetics having both high improvement effects on damaged hair and excellent sensation upon use, and a production method of the same.

The oil-based hair cosmetic material of the invention is those which comprise (A) a dibasic acid ester compound of general formula (1):

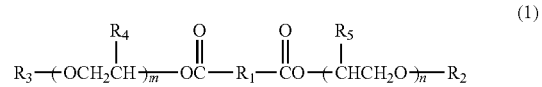

wherein $R_1$ is an alkylene group having a carbon number of 2-4, which may be mono- or poly-substituted, $R_2$ and $R_3$ are, independently of one another, an alkyl group having a carbon number of 1-4, which may be mono- or poly-substituted, $R_4$ and $R_5$ are, independently of one another, hydrogen or a methyl group or ethyl group which may be mono- or poly-substituted, m and n are, independently of one another, an integer of 0-4 with $m+n \geq 1$ (provided that the cases wherein $R_2$ and $R_3$ are both an ethyl group and m and n are both 1 are excluded), and (B) one or more oil agents selected from the group consisting of a volatile oil, an ester oil, a hydrocarbon oil, an animal/plant oil, and a silicone oil. Using this, it is possible to realize hair cosmetic materials and hair cosmetics that have both high improvement effects on damaged hair and excellent sensation upon use.

10 Claims, No Drawings

OILY HAIR COSMETICS

TECHNICAL FIELD

The present invention relates to an oil-based hair cosmetic material which provides excellent care for damaged hair and imparts comfortable sensation upon use. More specifically, the invention relates to an oil-based hair cosmetic material comprising a specific dibasic acid ester compound and a specific oil agent, that can improve surface and internal conditions of damaged hair, and impart comfortable sensation upon use by strengthening hair and achieving a non-sticky light finish, and also to a method for preparing the same.

BACKGROUND ART

In recent years, one of the major concerns in hair-care products is improvement in hair damages on surface of hair (cuticle), caused by outflow of internal lipids and the like due to chemical treatments including hair colors and permanent waves, and physical treatments including blowing; that is, for example, prevention of lifting up of cuticle, improvement in hair strength and smoothness, and prevention of hair dryness.

To improve conditions of damaged hair, there has been conventionally proposed a method to supplement an appropriate amount of oil to hair to provide the hair with smoothness and flexibility, by means of combining a plant oil such as camellia oil and olive oil to hair cosmetics.

Furthermore, to improve comfortable sensation upon use of hair cosmetics, concomitant use of silicone oils and their derivatives such as high-molecular-weight silicone oils and volatile silicone oils has also been proposed.

Moreover, to improve comfortable sensation upon use, concomitant use of ester oils such as diethoxy ethyl succinate has been proposed; also, aromatic alcohols such as benzyl alcohol have been used as a penetration-enhancing agent for oil agents.

However, when a plant oil alone is used as an ingredient of hair cosmetic materials for caring damaged hair, uncomfortable stickiness accompanies upon application to hair, and a heavy finish is also imparted; therefore, an entirely satisfactory hair cosmetic material could not be obtained.

Furthermore, even when a silicone oil is co-used, although a light refreshing finish is imparted, an improvement in hair strength is not sufficient, and unnatural shine deteriorates the hair appearance upon its application; thus, an entirely satisfactory hair cosmetic material could not be obtained in this case as well.

Moreover, concomitant use of conventional ester oils is not satisfactory from the viewpoint of improvement in sensation upon use, in addition to the problem of deteriorated storage stability. When aromatic alcohols are used as a penetration-enhancing agent, there is a problem of odor and safety, etc.; thus, an entirely satisfactory hair cosmetic material could not be obtained in this case as well.

For example, to improve sensation upon use, an oil-based hair cosmetic material formulated with a volatile hydrocarbon oil, a plant oil, and dimethiconol has been proposed (Patent Literature 1). To improve the effects of care for damaged hair and sensation upon use, a hair cosmetic material formulated with dimethyl polysiloxane and a hydrocarbon oil, etc. (Patent Literature 2), and an oil-based hair cosmetic material formulated with polyurethane polymer, a silicone oil and a nonionic surfactant, etc. (Patent Literature 3) have been proposed.

Further, in order to improve sensation upon use, a cosmetic material formulated with a diester of cyclohexanedicarboxylic acid and polyoxyethylene monoalkyl ether (Patent Literature 4), and a cosmetic material including hair conditioners, etc. that is formulated with polyoxyethylene dicarboxylate ester (Patent Literature 5), and a hair cosmetic material formulated with dialkylene glycol monoalkyl ether (Patent Literature 6) have been proposed.

However, in any of the above Patent Literatures, the oil-based hair cosmetic material of the present invention comprising a specific dibasic acid ester compound and a specific oil agent has not been disclosed; in addition, any of the cosmetic materials disclosed in the above Patent Literatures have not been sufficiently investigated or confirmed in terms of their effects as a hair cosmetic material from the viewpoints of both the care for damaged hair and improvement in sensation upon use.

In Patent Literature 7, an invention of oil agents and others comprising a specific dibasic acid ester compound has been disclosed, and a composition comprising said oil agent has been described; however, the structure and application of this invention relate to an aqueous cosmetic, and the object of the invention is to improve the sensation of use upon application to skin. Thus, the structure, application, object and effects of the invention differ from those in the present invention. There is also no description or suggestion regarding the effects of the oil-based hair cosmetic material used in the present invention that comprises a specific dibasic acid ester compound and a specific oil agent.

As mentioned above, to date there is no oil-based hair cosmetic materials that can improve surface and internal conditions of damaged hair and add strength to the hair, with comfortable sensation upon use by achieving a non-sticky and light finish, and there is no oil-based hair cosmetic materials that enable the production of hair cosmetics having such effects. In other words, at present, hair cosmetic materials that provide excellent care for damaged hair tend to have inferior sensation upon use.

Accordingly, the development of technology and products to realize hair cosmetic materials having both superior improving effects on damaged hair and excellent sensation upon use has been strongly desired.

CITATION LIST

Patent Literature
[Patent Literature 1] JP A No. 2008-273902
[Patent Literature 2] JP A No. 2008-174496
[Patent Literature 3] JP A No. 2008-137916
[Patent Literature 4] JP A No. 2008-127342
[Patent Literature 5] JP A No. 2001-226235
[Patent Literature 6] JP A No. Hei5-163120
[Patent Literature 7] WO 2008/096845

SUMMARY OF INVENTION

Technical Problem

The object of the present invention is to provide an oil-based hair cosmetic material that improves surface and internal conditions of damaged hair, adds strength and natural shine to the hair, provides a non-sticky light finish and prevents static electricity, thereby achieving comfortable sensation upon use, and to provide a method for preparing such oil-based hair cosmetic material.

Solution to Problem

As a result of intensive investigations taking into account the above-mentioned object, the present inventors have found that a specific dibasic acid ester compound has very superior characteristics as a penetration-enhancing agent for hair cosmetic materials, such as high permeability to hair, excellent safety, and almost no odor. In addition, by combining such a dibasic acid ester compound with a specific oil agent to formulate an oil-based hair cosmetic material, the inventors have found that the resulting hair cosmetic material has better effects in improving surface and internal conditions of damaged hair, adds strength and natural shine to the hair, provides a non-sticky light finish and prevents static electricity, thereby achieving comfortable sensation upon use; after further investigations, the inventors have accomplished the present invention.

Namely, the present invention relates to an oil-based hair cosmetic material comprising (A) a dibasic acid ester compound of general formula (1):

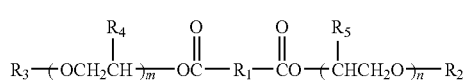
(1)

wherein $R_1$ is an alkylene group having a carbon number of 2-4, which may be mono- or poly-substituted, $R_2$ and $R_3$ are, independently of one another, an alkyl group having a carbon number of 1-4, which may be mono- or poly-substituted, $R_4$ and $R_5$ are, independently of one another, hydrogen or a methyl group or ethyl group which may be mono- or poly-substituted, m and n are, independently of one another, an integer of 0-4 with $m+n \geq 1$ (provided that the cases wherein $R_2$ and $R_3$ are both an ethyl group and m and n are both 1 are excluded), and (B) one or more oil agents selected from the group consisting of a volatile oil, an ester oil, a hydrocarbon oil, an animal/plant oil, and a silicone oil.

The invention also relates to said oil-based hair cosmetic material, wherein a poly- (or mono-)ethylene glycol monoether or a derivative thereof constituting the dibasic acid ester compound is one or more substances selected from the group consisting of diethylene glycol monoethyl ether, diethylene glycol monopropyl ether, diethylene glycol monoisopropyl ether, triethylene glycol monoethyl ether, triethylene glycol monopropyl ether, triethylene glycol monoisopropyl ether, dipropylene glycol monoethyl ether, dipropylene glycol monopropyl ether, dipropylene glycol monoisopropyl ether, tripropylene glycol monoethyl ether, tripropylene glycol monopropyl ether, tripropylene glycol monoisopropyl ether, dibutylene glycol monoethyl ether, dibutylene glycol monopropyl ether, dibutylene glycol monoisopropyl ether, dibutylene glycol monobuthyl ether, dibutylene glycol monoisobutyl ether, tributylene glycol monoethyl ether, tributylene glycol monopropyl ether, tributylene glycol monoisopropyl ether, tributylene glycol monobutyl ether, and tributylene glycol monoisobutyl ether.

Furthermore, the invention relates to said oil-based hair cosmetic material, wherein a dibasic acid constituting the dibasic acid ester compound is malic acid or succinic acid.

In addition, the invention relates to said oil-based hair cosmetic material, wherein the dibasic acid ester compound is bis-diethylene glycol ethyl ether succinate (bis-ethoxydiglycol succinate).

Furthermore, the invention relates to said oil-based hair cosmetic material, wherein the oil-based hair cosmetic material comprises 1.0-50% by mass of the dibasic acid ester compound based on the total mass of the oil-based hair cosmetic material.

In addition, the invention relates to said oil-based hair cosmetic material, wherein the oil-based hair cosmetic material comprises 0.1-99% by mass of the oil agent based on the total mass of the oil-based hair cosmetic material.

Furthermore, the invention relates to a hair cosmetic comprising any of the above-described oil-based hair cosmetic materials.

In addition, the invention relates to said hair cosmetic, wherein the hair cosmetic is selected from the group consisting of hair oil, hair liquid, hair gel, hair spray, hair stick and hair mousse.

Furthermore, the invention relates to a method for preparing any of the above-described oil-based hair cosmetic materials or hair cosmetics, comprising a step of mixing a dibasic acid ester compound with one or more oil agents.

With respect to the oil-based hair cosmetic material of the present invention, the mechanism with which effects of improving both damaged hair and sensation upon use are enhanced by means of concomitant use of a specific dibasic acid ester compound and a specific oil agent, compared to conventional hair cosmetic materials, has not yet been thoroughly clarified.

The specific dibasic acid ester compound used in the oil-based hair cosmetic material of the present invention is a penetration-enhancing agent that has particularly excellent characteristics of both water solubility and oil solubility compared to conventional penetration-enhancing agents; accordingly, said compound has high compatibility with both the hair which comprises proteins and water and has high polarity, and the oil agent formulated as an ingredient for caring damaged hair.

Due to such characteristics, it is considered that the dibasic acid ester compound of the invention suppresses lifting up of cuticle on the surface of damaged hair, and fills the voids from which internal lipid of the hair has flown out, thereby giving an appropriate amount of oil to the hair to increase its strength as well as to prevent evaporation of water content and generation of static electricity; in addition, it also prevents attachment of an excessive amount of an oil agent to the hair surface to achieve a non-sticky light finish and natural shine.

Advantageous Effects Of Invention

The oil-based hair cosmetic material of the invention has the following effects: compared to conventional hair cosmetic materials, it improves conditions of damaged hair, and it imparts strength and natural shine to hair and achieves a non-sticky light finish and prevents generation of static electricity, thereby exhibiting superior sensation upon use. Of the oil-based hair cosmetic materials of the invention, those wherein the dibasic acid ester compound is bis-diethylene glycol succinate ethyl ether (bis-ethoxydiglycol succinate) are particularly superior in the effects of improving damaged hair and in their comfortable sensation upon use.

Thus, the oil-based hair cosmetic materials of the invention can be applied to wide range of hair cosmetics including hair oil, hair liquid, hair gel, hair spray, hair stick and hair mousse, and such hair cosmetics containing the oil-based hair cosmetic materials of the invention are expected to show various effects including excellent sensation upon use.

DESCRIPTION OF EMBODIMENTS

As used herein, "hair cosmetic" is not particularly limited, and means any products used for hairdressing, washing and caring for hair of humans. The hair cosmetic of the invention encompasses products used for washing, caring and treating head of hair, scalp, root of hair, body hair and body skin of humans and animals. Specific preferred examples include oil-based hair cosmetics used for hairdressing and caring for head of hair of humans.

As used herein, "hair cosmetic material" is not particularly limited, and means any compositions used for the preparation of the above hair cosmetics.

Furthermore, as used herein, "oil-based hair cosmetic material" and "oil-based hair cosmetic" are not particularly limited, and they mean any hair cosmetic materials and hair cosmetics comprising a substance with an oil-soluble characteristic as a main ingredient. Specific preferred examples include non-aqueous oil-based hair cosmetic materials and oil-based hair cosmetics wherein substantially no water is formulated.

In the oil-based hair cosmetic material of the invention, the dibasic acid ester compound used as a penetration-enhancing agent for hair is a dibasic acid ester compound of general formula (1) below:

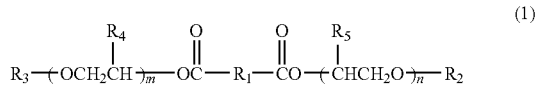

(1)

In the above general formula (1), $R_1$ is an alkylene group having a carbon number of 2-4, which may be mono- or poly-substituted, $R_2$ and $R_3$ are, independently of one another, an alkyl group having a carbon number of 1-4, which may be mono- or poly-substituted, $R_4$ and $R_5$ are, independently of one another, hydrogen or a methyl group or ethyl group which may be mono- or poly-substituted, m and n are, independently of one another, an integer of 0-4 with m+n≥1 (provided that the cases wherein $R_2$ and $R_3$ are both an ethyl group and m and n are both 1 are excluded).

Here, the carbon number of $R_1$ is, from the viewpoints of hair permeability and others, preferably 2 or 3; the carbon numbers of $R_2$ and $R_3$ are, from the viewpoints of hair permeability, improvement effect on damaged hair and others, preferably and independently of one another, from 2 to 4; m and n are, from the viewpoints of hair permeability, improvement effect on damaged hair and others, preferably and independently of one another, 2 or 3.

In addition, the types of $R_4$ and $R_5$ are, from the viewpoint of better balance between water solubility and oil solubility, preferably hydrogen.

Each of the functional groups $R_1$-$R_5$ may, depending on the application of the oil-based hair cosmetic material of the invention, be mono- or poly-substituted in order to adjust water solubility and oil solubility, and examples of said substituents include hydroxyl group, alkoxy group, substituted or unsubstituted amino group, and ester group, etc.

From the viewpoints of organic synthesis and others, the carbon numbers of $R_2$ and $R_3$, the values of n and m, and the types of $R_4$ and $R_5$ are preferably the same each other.

The oil-based hair cosmetic material of the invention may use an ester compound of the above general formula (1) alone, or a combination of two or more of said compounds.

Specific examples of $R_1$ include ethylene, propylene, isopropylene, butylene, isobutylene, etc.; preferably, they include ethylene, propylene and isopropylene.

Specific examples of $R_2$ and $R_3$ include methyl group, ethyl group, n-propyl group, isopropyl group, n-butyl group, isobutyl group, sec-butyl group, tert-butyl group, etc.; preferably, they include ethyl group, n-propyl group, isopropyl group, n-butyl group, and isobutyl group. Alkyl groups represented by $R_2$ and $R_3$ may be the same or different each other.

In the above general formula (1), a poly- (or mono-)ethylene glycol monoether or a derivative thereof constituting the dibasic acid ester compound, namely, $R_2(OCH_2CHR_5)_nOH$ and $R_3(OCH_2CHR_4)_mOH$ may be the same or different each other; specific preferred examples include, for example, diethylene glycol monoethyl ether, diethylene glycol monopropyl ether, diethylene glycol monoisopropyl ether, diethylene glycol monoisobutyl ether, triethylene glycol monoethyl ether, triethylene glycol monopropyl ether, triethylene glycol monoisopropyl ether, triethylene glycol monoisobutyl ether, propylene glycol monomethyl ether, propylene glycol monoethyl ether, propylene glycol monopropyl ether, propylene glycol monoisopropyl ether, propylene glycol monobutyl ether, propylene glycol monoisobutyl ether, dipropylene glycol monomethyl ether, dipropylene glycol monoethyl ether, dipropylene glycol monopropyl ether, dipropylene glycol monoisopropyl ether, dipropylene glycol monobutyl ether, dipropylene glycol monoisobutyl ether, tripropylene glycol monomethyl ether, tripropylene glycol monoethyl ether, tripropylene glycol monopropyl ether, tripropylene glycol monoisopropyl ether, tripropylene glycol monobutyl ether, tripropylene glycol monoisobutyl ether, tetrapropylene glycol monomethyl ether, tetrapropylene glycol monoethyl ether, tetrapropylene glycol monopropyl ether, tetrapropylene glycol monoisopropyl ether, tetrapropylene glycol monobutyl ether, tetrapropylene glycol monoisobutyl ether, butylene glycol monomethyl ether, butylene glycol monoethyl ether, butylene glycol monopropyl ether, butylene glycol monoisopropyl ether, butylene glycol monobutyl ether, butylene glycol monoisobutyl ether, dibutylene glycol monomethyl ether, dibutylene glycol monoethyl ether, dibutylene glycol monopropyl ether, dibutylene glycol monoisopropyl ether, dibutylene glycol monobutyl ether, dibutylene glycol monoisobutyl ether, tributylene glycol monomethyl ether, tributylene glycol monoethyl ether, tributylene glycol monopropyl ether, tributylene glycol monoisopropyl ether, tributylene glycol monobutyl ether, tributylene glycol monoisobutyl ether, tetrabutylene glycol monomethyl ether, tetrabutylene glycol monoethyl ether, tetrabutylene glycol monopropyl ether, tetrabutylene glycol monoisopropyl ether, tetrabutylene glycol monobutyl ether, and tetrabutylene glycol monoisobutyl ether, etc.; from the viewpoints of hair permeability, improvement effect on damaged hair and others, more preferred specific examples include diethylene glycol monoethyl ether, diethylene glycol monopropyl ether, diethylene glycol monoisopropyl ether, triethylene glycol monoethyl ether, triethylene glycol monopropyl ether, triethylene glycol monoisopropyl ether, dipropylene glycol monoethyl ether, dipropylene glycol monopropyl ether, dipropylene glycol monoisopropyl ether, tripropylene glycol monoethyl ether, tripropylene glycol monopropyl ether, tripropylene glycol monoisopropyl ether, dibutylene glycol monoethyl ether, dibutylene glycol monopropyl ether, dibutylene glycol monoisopropyl ether, dibutylene glycol monobuthyl ether, dibutylene glycol monoisobutyl ether, tributylene glycol monoethyl ether, tributylene glycol monopropyl ether, tributylene glycol monoisopropyl ether, tributylene glycol monobutyl ether, tributylene glycol monoisobutyl ether, etc.; from the viewpoint of more superior balance between water solubility and oil solubility, more preferred specific examples include diethylene glycol monoethyl ether, diethylene glycol monopropyl ether, diethylene glycol monoisopropyl ether, triethylene glycol monoethyl ether, triethylene glycol monopropyl ether, triethylene glycol monoisopropyl ether, etc., and particularly preferred specific examples include diethylene glycol monoethyl ether.

From the viewpoints of organic synthesis and others, the above $R_2$ and $R_3$, as well as $R_2 (OCH_2CHR_5)_n OH$ and $R_3 (OCH_2CHR_4)_m OH$ may preferably be the same each other.

Examples of a dibasic acid constituting the ester compounds of the above general formula (1) are dibasic acids having a carbon number of 2-4, and include, preferably, malic acid, succinic acid, tartaric acid and adipic acid, etc. From the viewpoints of hair permeability and others, more preferably they include succinic acid and malic acid.

Specific preferred examples of dibasic acid ester compounds wherein each $R_4$ and $R_5$ is hydrogen include, for example, bis-ethylene glycol ethyl ether succinate, bis-diethylene glycol ethyl ether succinate (bis-ethoxydiglycol succinate), bis-triethylene glycol ethyl ether succinate, bis-ethylene glycol propyl ether succinate, bis-diethylene propyl ether glycol succinate, bis-triethylene glycol propyl ether succinate, bis-ethylene glycol isopropyl ether succinate, bis-diethylene glycol isopropyl ether succinate, bis-triethylene glycol isopropyl ether succinate, bis-ethylene glycol isobutyl ether succinate, bis-diethylene glycol isobutyl ether succinate, bis-triethylene glycol isobutyl ether succinate, bis-ethylene glycol ethyl ether malate, bis-diethylene glycol ethyl ether malate, bis-triethylene glycol ethyl ether malate, bis-ethylene glycol propyl ether malate, bis-diethylene glycol propyl ether malate, bis-triethylene glycol propyl ether malate, bis-ethylene glycol isopropyl ether malate, bis-diethylene glycol isopropyl ether malate, bis-triethylene glycol isopropyl ether malate, bis-ethylene glycol isobutyl ether malate, bis-diethylene glycol isobutyl ether malate, bis-triethylene glycol isobutyl ether malate,
bis-ethylene glycol ethyl ether tartrate, bis-diethylene glycol ethyl ether tartrate, bis-triethylene glycol ethyl ether tartrate, bis-ethylene glycol propyl ether tartrate, bis-diethylene glycol propyl ether tartrate, bis-triethylene glycol propyl ether tartrate, bis-ethylene glycol isopropyl ether tartrate, bis-diethyleneglycol isopropyl ether tartrate, bis-triethylene glycol isopropyl ether tartrate, bis-ethylene glycol isobutyl ether tartrate, bis-diethylene glycol isobutyl ether tartrate, bis-triethylene glycol isobutyl ether tartrate, bis-ethylene glycol ethyl ether adipate, bis-diethylene glycol ethyl ether adipate, bis-triethylene glycol ethyl ether adipate, bis-ethylene glycol propyl ether adipate, bis-diethylene glycol propyl ether adipate, bis-triethylene glycol propyl ether adipate, bis-ethylene glycol isopropyl ether adipate, bis-diethylene glycol isopropyl ether adipate, bis-triethylene glycol isopropyl ether adipate, bis-ethylene glycol isobutyl ether adipate, bis-diethylene glycol isobutyl ether adipate, bis-triethylene glycol isobutyl ether adipate, etc. More preferred specific examples include bis-diethylene glycol ethyl ether succinate (bis-ethoxydiglycol succinate), bis-triethylene glycol ethyl ether succinate, bis-triethylene glycol propyl ether succinate, bis-diethylene glycol ethyl ether malate, bis-triethylene glycol ethyl ether malate, etc. Particularly preferred specific examples include bis-diethylene glycol ethyl ether succinate (bis-ethoxydiglycol succinate).

Specific preferred examples of dibasic acid ester compounds wherein each $R_4$ and $R_5$ is a methyl group include, for example, bis-propylene glycol ethyl ether succinate, bis-dipropylene glycol ethyl ether succinate, bis-tripropylene glycol ethyl ether succinate, bis-propylene glycol propyl ether succinate, bis-dipropylene glycol propyl ether succinate, bis-tripropylene glycol propyl ether succinate, bis-propylene glycol isopropyl ether succinate, bis-dipropylene glycol isopropyl ether succinate, bis-tripropylene glycol isopropyl ether succinate, bis-propylene glycol isobutyl ether succinate, bis-dipropylene glycol isobutyl ether succinate, bis-tripropylene glycol isobutyl ether succinate, bis-propylene glycol ethyl ether malate, bis-dipropylene glycol ethyl ether malate, bis-tripropylene glycol ethyl ether malate, bis-propylene glycol propyl ether malate, bis-dipropylene glycol propyl ether malate, bis-tripropylene glycol propyl ether malate, bis-propylene glycol isopropyl ether malate, bis-dipropylene glycol isopropyl ether malate, bis-tripropylene glycol isopropyl ether malate, bis-propylene glycol isobutyl ether malate, bis-dipropylene glycol isobutyl ether malate, bis-tripropylene glycol isobutyl ether malate, bis-propylene glycol ethyl ether tartrate, bis-dipropylene glycol ethyl ether tartrate, bis-tripropylene glycol ethyl ether tartrate, bis-propylene glycol propyl ether tartrate, bis-dipropylene glycol propyl ether tartrate, bis-tripropylene glycol propyl ether tartrate, bis-propylene glycol isopropyl ether tartrate, bis-dipropylene glycol isopropyl ether tartrate, bis-tripropylene glycol isopropyl ether tartrate, bis-propylene glycol isobutyl ether tartrate, bis-dipropylene glycol isobutyl ether tartrate, bis-tripropylene glycol isobutyl ether tartrate, bis-propylene glycol ethyl ether adipate, bis-dipropylene glycol ethyl ether adipate, bis-tripropylene glycol ethyl ether adipate, bis-propylene glycol propyl ether adipate, bis-dipropylene glycol propyl ether adipate, bis-tripropylene glycol propyl ether adipate, bis-propylene glycol isopropyl ether adipate, bis-dipropylene glycol isopropyl ether adipate, bis-tripropylene glycol isopropyl ether adipate, bis-propylene glycol isobutyl ether adipate, bis-dipropylene glycol isobutyl ether adipate, bis-tripropylene glycol isobutyl ether adipate, etc. More preferred specific examples include bis-tripropylene glycol ethyl ether succinate, bis-tripropylene glycol isopropyl ether succinate, bis-tripropylene glycol isopropyl ether malate, etc.

Specific preferred examples of dibasic acid ester compounds wherein each $R_4$ and $R_5$ is an ethyl group include, for example, bis-butylene glycol ethyl ether succinate, bis-dibutylene glycol ethyl ether succinate, bis-tributylene glycol ethyl ether succinate, bis-butylene glycol propyl ether succinate, bis-di butylene glycol propyl ether succinate, bis-tributylene glycol propyl ether succinate, bis-butylene glycol isopropyl ether succinate, bis-dibutylene glycol isopropyl ether succinate, bis-tributylene glycol isopropyl ether succinate, bis-butylene glycol isobutyl ether succinate, bis-dibutylene glycol isobutyl ether succinate, bis-tributylene glycol isobutyl ether succinate, bis-butylene glycol ethyl ether malate, bis-dibutylene glycol ethyl ether malate, bis-tributylene glycol ethyl ether malate, bis-butylene glycol propyl ether malate, bis-dibutylene glycol propyl ether malate, bis-tributylene glyco propyl ether 1 malate, bis-butylene glycol isopropyl ether malate, bis-dibutylene isopropyl ether glycol malate, bis-tributylene glycol isopropyl ether malate, bis-butylene glycol isobutyl ether malate, bis-dibutylene glycol isobutyl ether malate, bis-tributylene glycol isobutyl ether malate, bis-butylene glycol ethyl ether tartrate, bis-dibutylene glycol ethyl ether tartrate, bis-tributylene glycol ethyl ether tartrate, bis-butylene glycol propyl ether tartrate, bis-dibutylene glycol propyl ether tartrate, bis-tributylene glycol propyl ether tartrate, bis-butylene glycol isopropyl ether tartrate, bis-dibutylene glycol isopropyl ether tartrate, bis-tributylene glycol isopropyl ether tartrate, bis-butylene glycol isobutyl ether tartrate, bis-dibutylene glycol isobutyl ether tartrate, bis-tributylene glycol isobutyl ether tartrate, bis-butylene glycol ethyl ether adipate, bis-dibutylene glycol ethyl ether adipate, bis-tributylene glycol ethyl ether adipate, bis-butylene glycol propyl ether adipate, bis-dibutylene glycol propyl ether adipate, bis-tributylene glycol propyl ether adipate, bis-butylene glycol isopropyl ether adipate, bis-dibutylene glycol isopropyl ether adipate, bis-tributylene glycol isopropyl ether adipate, bis-butylene glycol isobutyl ether adipate, bis-dibutylene glycol isobutyl ether adipate, bis-tributylene glycol isobutyl ether adipate, etc. More preferred specific examples include bis-tributylene glycol ethyl ether succinate, bis-tributylene glycol isobutyl ether succinate, bis-dibutylene glycol isobutyl ether malate, bis-tributylene glycol isobutyl ether malate, etc.

The amount of an ester compound of the above general formula (1) contained in the total mass of the oil-based hair cosmetic material is, preferably 1-50 mass %, more preferably 2-45 mass %, furthermore preferably 3-40 mass %, and particularly preferably 5-35 mass %. When the amount of an ester compound is too low, then sufficient penetration-enhancing effect cannot be obtained and the improvement effect on damaged hair tends to deteriorate; whereas when the amount of an ester compound is too high, sensation upon application to hair as well as after application tends to deteriorate (stickiness tends to increase), and the effect obtained is smaller relative to its amount contained, which is uneconomical. Thus, the amount within the above range is preferable because sufficient improvement effect of damaged hair as well as excellent sensation upon use and economic efficiency can be obtained.

The oil agent used in the oil-based hair cosmetic material of the invention is a volatile oil, an ester oil, a hydrocarbon oil, an animal/plant oil, or a silicone oil. From the viewpoints of individual difference in hairs, degree of damage, and wide range of application, it is preferable that two or more of these oil agents are mixed for use. Specific examples of the oil agent used in the invention include the following.

Specific preferred examples of volatile oils include, for example, isododecane, isohexadecane, cyclic silicone oils such as decamethylcyclopentasiloxane, etc.

Of the above volatile oils, from the viewpoints of sensation upon use at the time of application to hair as well as after its volatilization, more preferred specific examples include, for example, isododecane and isohexadecane, etc.

Specific preferred examples of ester oils include the following: for example, as monoesters, isononanoates such as isononyl isononanoate and isotridecyl isononanoate, etc., 2-ethylhexanoate such as cetyl ethylhexanoate and hexyldecyl ethylhexanoate, etc., myristates such as isopropyl myristate, isocetyl myristate, octyldodecyl myristate, etc., isostearates such as ethyl isostearate, isopyropyl isostearate, hexyldecyl isostearate, isostearyl isostearate, cholesteryl isostearate, phytosteryl isostearate, etc., lactates such as isostearyl lactate, octyldodecyl lactate, etc., hydroxystearates such as ethylhexyl hydroxystearate, octyl hydroxystearate, phytosteryl hydroxystearate, cholesteryl hydroxystearate, etc., oleates such as oleyl oleate, phytosteryl oleate, octyldodecyl oleate, etc., neopentanoates such as isodecyl neopentanoate, isostearyl neopentanoate, etc., palmitates such as isopyropyl palmitate, ethylhexyl palmitate, etc., and octyldodecyl neodecanoate, octyldodecyl ricinoleate, oleyl erucate, octyldodecyl erucate, isopropyl lauroylsarcosinate, etc.

Diester oils include diisobutyl adipate, diisopropyl adipate, diethylhexyl succinate, neopentyl glycol diisononanoate, neopentyl glycol diethyl hexanoate, neopentyl glycol dicaprate, diisostearyl malate, diisopropyl dilinoleate, ethylene glycol dioctanoate, octyldodecyl stearoyloxystearate, diisopropyl sebacate, di(cholesteryl/octyldodecyl) lauroyl glutamate, di(phytosteryl/octyldodecyl) lauroyl glutamate, etc.

Triester oils include triethyl hexanoin, trimethylolpropane triethylhexanoate, caprylic/capric triglyceride, triisostearin, trimethylolpropane triisostearate, etc.

Tetraester oils include pentaerythrityl tetraethylhexanoate, pentaerythrityl tetraisostearate, etc.

Polyester oils include polyglycerin fatty acid esters such as polyglyceryl-2 isostearate, polyglyceryl-2 diisostearate, polyglyceryl-2 triisostearate, polyglyceryl-2 tetraisostearate, etc.

High-viscosity ester oils include dipentaerythrityl hexa (hydroxystearate/stearate/rosinate), hydrogenated castor oil isostearate, hydrogenated castor oil dimer dilinoleate, (polyglyceryl-2 isostearate/dimer dilinoleate) copolymer, (phytosteryl/isostearyl/cetyl/stearyl/behenyl) dimer dilinoleate, bis (phytosteryl/behenyl/isostearyl) dimer dilinoleyl dimer dilinoleate, di(isostearyl/phytosteryl) dimer dilinoleate, dimer dilinoleyl hydrogenated rosin condensation product, dimer dilinoleyl diisostearate, dimer dilinoleyl dimer dilinoleate, di(cholesteryl/behenyl/octyldodecyl) lauroyl glutamate, di(octyldodecyl/phytosteryl/behenyl) lauroyl glutamate, myristoyl methylalanine (phytosteryl/decyl tetradecyl), (diglycerin/dilinoleate/hydroxystearate) copolymer, etc.

Of the above ester oils, from the viewpoints of improvement in hair strength and others, more preferred specific examples include, for example, (polyglyceryl-2 isostearate/ dimer dilinoleate) copolymer, hydrogenated castor oil isostearate, (diglycerin/dilinoleate/hydroxystearate) copolymer, dipentaerythrityl hexa(hydroxystearate/stearate/rosinate), etc.

Specific preferred examples of hydrocarbon oils include, for example, ozokerite, squalane, squalene, ceresin, paraffin, isoparaffin, paraffin wax, liquid paraffin, pristane, polyisobutylene, polyisobutene, hydrogenated polyisobutene, microcrystalline wax, polyethylene wax, and vaselline, etc.

Of the above hydrocarbon oils, from the viewpoint of sensation upon use at the time of application to hair, more preferred specific examples include, for example, squalane and liquid paraffin, etc.

Specific preferred examples of higher fatty acids include, for example, lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, etc.

Of the above higher fatty acids, from the viewpoint of sensation upon use at the time of application to hair, more preferred specific examples include, for example, isostearic acid, etc.

Specific preferred examples of animal/plant oils and hydrogenated animal/plant oils include, for example, avocado oil, perilla oil, olive oil, cocoa butter, Japanese Torreya oil, apricot kernel oil, hydrogenated oil, wheat germ oil, sesame oil, rice germ oil, rice bran oil, sugarcane wax, sasanqua oil, safflower oil, shea butter, Paulownia (wood) oil, cinnamon oil, soybean oil, tea seed oil, camellia oil, evening primrose oil, corn oil, rapeseed oil, germ oil, palm oil, palm kernel oil, castor oil, hydrogenated castor oil, sunflower oil, grape oil, jojoba oil, macadamia nut oil, bees wax, cotton seed oil, cotton wax, Japan wax, montan wax, coconut oil, hydrogenated coconut oil, groundnut oil, lanolin, liquid lanolin, reduced lanolin, lanolin alcohol, hard lanolin, lanolin acetate, lanolin fatty acid isopropyl, hexyl laurate, etc.

Of the above animal/plant oils and hydrogenated animal/ plant oils, from the viewpoints of sensation upon use (easy application) and imparting flexibility to hair, more preferred specific examples include, for example, camellia oil, rice bran oil, jojoba oil and shea butter, etc.

Specific preferred examples of silicone oils include, for example, silicone compounds such as dimethyl polysiloxane, methylphenyl polysiloxane, alkyl-modified organopolysiloxane, end-modified organopolysiloxane, fluorine-modified organopolysiloxane, amodimethicone, amino-modified organopolysiloxane, volatile silicone, alkyldimethicone, etc.

Of the above silicone oils, from the viewpoints of sensation upon use at the time of application to hair and after application (light finish and smoothness of hair), more preferred specific examples include, for example, dimethyl polysiloxane and volatile silicone, etc.

The amount of the above oil agents contained in the total mass of the oil-based hair cosmetic material is, preferably 0.1-99 mass %, more preferably 1-95 mass %, and furthermore preferably 5-90 mass %. When the amount of an oil agent is too low, then the improvement effect on damaged hair tends to deteriorate; whereas when the amount of an oil agent is too high, sensation upon use tends to deteriorate and a heavier hair finish tends to result (hair appearance after finish is not good). Thus, when the amount contained is within the above range, sufficient improvement effect on damaged hair as well as excellent sensation upon use can be obtained.

The oil-based hair cosmetic material of the invention may comprise other ingredients that are generally used in the field of hair cosmetics, within a range that does not deteriorate the effects of the invention. Other ingredients includes alcohols, multivalent alcohols, thickeners, anionic surfactants, non-ionic surfactants, moisturizing agents, plant extracts, dye-stuffs, pigments, antiseptic agents, chelating agents, antioxidant agents, ultraviolet absorbers, and perfumes, etc. One or more of these ingredients may be appropriately formulated.

Alcohols preferably used in the invention are not particularly limited, and include the following.

As branched alcohols, they include those having a carbon number of 10-40, such as hexyl decanol, isostearyl alcohol, octyl dodecanol, decyl tetradecanol, dodecyl hexadecanol, tetradecyl octadecanol, hexadecyl eicosanol, etc., and more preferably, octyl dodecanol, etc.

As divalent alcohols, they include butylene glycol, pentylene glycol, propylene glycol, dipropylene glycol, hexylene glycol, octylene glycol, and polypropylene glycols having an average molecular weight of 200-2000.

As higher alcohols, those having a carbon number of 7 or more are preferred, and more preferably those with a carbon number of 10 or more, and furthermore preferably those with a carbon number of 15 or more. Specific examples include lauryl alcohol, myristyl alcohol, stearyl alcohol, eicosanol, behenyl alcohol, oleyl alcohol, cetostearyl alcohol, cholesterol, phytosterol, POE cholesterol ether, monostearyl glycerin ether (batyl alcohol), monooleyl gryceryl ether (selachyl alcohol), cetanol, etc.

Thickeners preferably used in the present invention are not particularly limited, and they include natural and artificial thickeners, for example, alginic acid, polyaspartic acid, deoxyribonucleic acid and its salts, guar gum, agar, gelatin, sodium polyacrylate, cellulose ester, calcium alginate, carboxyvinyl polymer, ethylene/acrylic acid copolymer, vinylpyrolidone polymers, vinyl alcohol/vinylpyrolidone copolymer, nitrogen-substituted acrylamide polymer, polyacrylamido, cationic guar gum, dimethylacryl ammonium polymer, acrylic acid/acryl methacrylate copolymer, POE/POP copolymer, polyvinyl alcohol, pullulan, tamarind seed polysaccharide, xanthan gum, carageenan, high-methoxyl pectin, low-methoxyl pectin, gum arabic, crystalline cellulose, arabinogalactan, karaya gum, gum tragacanth, albumin, casein, curdlan, gellan gum, dextrin fatty acid ester, cellulose, polyethyleneimine, high-polymerization-degree polyethylene glycol, cationic silicone polymer, synthetic latex, alkyldimethicone with a carbon number of 18 or more and silicone polyamide copolymer that is a silicon gelling agent, (behenic acid eicosandioic acid) glyceryl, (behenic acid eicosandioic acid) polyglyceryl-10, (vinyl caprolactam/VP/dimethylaminoethyl methacrylate) copolymer, etc.

When the oil-based hair cosmetic material of the invention is to be used for medicinal drugs and quasi drugs, depending on intended purposes or as necessary, it may comprise skin-whitening agents, moisturizing agents, antioxidants, anti-inflammatory agents, vitamins, enzymes, circulation promotion agents, amino acids, UV-absorbing agents, sunscreen agents, suntan agents, hair tonic agents (hair-loss prevention agents, hair growth promotion agents, etc.), animal or plant extracts, antiseptic agents, hair softeners, hair moisturizers, makeup preparations, hair conditioners, skin conditioners, hair whitening agents, chelating agents, cell replacement promotion agents, coloring agents, skin softening agents, skin moisturizing agents, deodorants, antiperspirants, etc. One or more of these ingredients may be appropriately formulated.

By formulating the oil-based hair cosmetic material of the invention into a hair cosmetic, the hair cosmetic with improvement effects on damaged hair and excellent sensation upon use can be obtained.

Forms of the hair cosmetic of the present invention is not particularly limited, and hair cosmetics may be formulated in a form appropriate for each application, selected from hair oil, hair liquid, hair gel, hair spray, hair stick and hair mousse, etc., such as a form of liquid, gel, wax, crème, multi-layered oil, pomade, stick, or mousse. Furthermore, depending on the combination with containers, they may be in a form of mist-type, hair spray, and aerosol, etc.

While the present invention relates also to a method for the preparation of oil-based hair cosmetic materials or hair cosmetics having superior effects on damaged hair with excellent sensation upon use, the method is not particularly limited, and may appropriately utilize publicly-known general methods; and the method comprises a step of mixing a dibasic acid ester compound of the above general formula (1) with one or more oil agents selected from the group consisting of a volatile oil, an ester oil, a hydrocarbon oil, an animal/plant oil and a silicone oil.

For instance, in cases where a gel-type oil-based hair cosmetic is prepared, a dibasic acid ester compound of the above general formula (1) of the invention and oil agents may be stirred together with alcohols and water-soluble polymers so that they are homogeneously dispersed, then the resulting mixture may be cooled into a gel form to give the hair cosmetic. A crème-type or emulsion-type oil-based hair cosmetic may be prepared as follows: a dibasic acid ester compound of the invention and oil agents are stirred with alcohols, multivalent alcohols, water-soluble polymers, and ingredients generally used in the field of cosmetics such as emulsifiers and solubilizing agents, so that the resulting mixture is emulsified, then it is cooled to become a crème-type or emulsion-type substance. Furthermore, a mousse-type or foam-type oil-based hair cosmetic may be prepared as follows: a dibasic acid ester compound of the invention and oil agents as well as a surfactant and a thickener (water-soluble polymer) are dissolved and dispersed, then it is filled into an aerosol can together with a liquefied petroleum gas (propellant); thus, upon usage, the resulting mixture is sprayed in a form of mousse or foam.

EXAMPLES

Hereinafter, the present invention is described further in detail using examples; however, the invention is not limited thereto.

Various modifications are possible within the technical idea of the present invention. Unless otherwise specified, "%" described below means "mass %."

Examples 1-8

(Preparation and Evaluation of Hair Oil)

Hair oils of Examples 1-8 and Comparative example 1 with the composition shown in Table 1 were prepared in accordance with the preparation method below. Properties of the hair oils of Examples 1-8 and Comparative example 1 were evaluated in accordance with the evaluation method below. Results are shown in Table 1.

(Preparation Method)

Ingredients of each composition listed in Table 1 were mixed, and dissolved by stirring at room temperature to give a homogeneous mixture; as a result, hair oils of Examples 1-8 and Comparative example 1 were obtained.

(Evaluation Method)

(1) Sensory Evaluation (a) Preparation of hair bundles for evaluation

Hair from Japanese adult women whose hair has not been chemically treated with perms and hair colors, etc. was subjected to damages by 3 times of bleaching treatments (brand name: Palty, from DARIYA), and 4 times of washing and drying by a dryer. Using this damaged hair, hair bundles for evaluation with a length of 10 cm, width of 3 cm, and weight of 6 g were prepared.

(b) Treatment of Hair Bundles for Evaluation

Each sample from Examples and Comparative example was taken by a finger in an amount of 0.5 g, and was homogeneously applied to one of the above hair bundles by spreading the sample using fingers, then the hair bundle was naturally dried. Next, the hair bundle after sample application was shampooed (brand name: TSUBAKI, from Shiseido Co., Ltd.), and dried using a dryer. To the hair bundles after shampooing, each 0.5-g sample from Examples and Comparative example was homogeneously applied and naturally dried. This procedure was repeated 5 times.

(c) Sensory Evaluation

With respect to each of the hair bundles for evaluation during and after the above treatment, 10 evaluation panelists rated the hair bundles in terms of 6 items below in accordance with the after-mentioned 5-grade evaluation standard, and their average values were obtained.

*Easy application (easiness of spreading)
*Non-stickiness
*Light finish/smoothness
*Easiness in taking shape
*Hair strength
*Natural shine (2) Storage Stability Each of the samples of Examples and Comparative example is comprehensively evaluated by the following two test methods:

1) a thermostatic storage test wherein samples are stored in a thermostatic chamber at 45° C. for 3 months, and
2) a cycle test wherein samples are stored under a cyclic condition comprising a) storage at −5° C. for 12 hours, b) heating to 25° C. and storage for 12 hours, c) heating to 45° C. and storage for 12 hours, d) cooling to 25° C. and storage for 12 hours, e) cooling to −5° C.; then this cyclic storage is repeated 5 times.

Samples were visually observed in terms of external appearances such as separation, perspiration and discoloration, and changes in the external appearances were subjected to sensory evaluation in accordance with the after-mentioned 5-grade evaluation standard.

(3) Improvement Effect on Cuticle

Regarding one each evaluation hair bundle treated with samples from the above Examples and Comparative example, condition of detachment of cuticles on hair surface as well as condition of lift-up of cuticles were observed and photographed using a field-emission-type scanning electron microscope (JSM-7000F, from JEOL Ltd.) to evaluate improvement effects on cuticle (improvement effects on damaged hair).

Condition of detachment of cuticles was evaluated as follows: the number of cuticle-detachment points at 5 representative positions on an arbitrary hair in each hair bundle was counted, and its average value was calculated and converted to 5-grade evaluation with the following criteria: score of 5 for cases without cuticle-detachment points, 4 for cases with one cuticle-detachment point, 3 for cases with two or three cuticle-detachment points, and 2 for cases with four or five cuticle-detachment points, and 1 for cases with six or more cuticle-detachment points.

Condition of lift-up of cuticles was evaluated as follows: a lift-up angle of cuticle (an angle formed between the cuticle lifted up and the hair surface) at 5 representative positions on an arbitrary hair in each hair bundle was measured, and its average value was calculated and converted to 5-grade evaluation with the following criteria: score of 5 for cases with cuticle-lift-up angle of 0°, 4 for cases with the angle greater than 0° but less than 1.0°, 3 for cases with the angle greater than 1.0° but less than 1.5°, 2 for cases with the angle greater than 1.5° but less than 2.0°, and 1 for cases with the angle greater than 2.0°.

(4) Antistatic Effect

For one each hair bundle treated using samples from the above Examples and Comparative example, static electricity was intentionally generated by rubbing the hair bundle with a plastic brush for 7 times from the root of the hair bundle to its tip. Then, static voltage of the surface of the hair bundle was measured using a static electrometer (SV-10, from Kasuga Electric Works Ltd.), and its average value was calculated and converted to 5-grade evaluation with the following criteria: score of 5 for cases with static voltage of less than 15 kV, 4 for cases with 15 kV or greater but less than 18 kV, 3 for cases with 18 kV or greater but less than 20 kV, 2 for cases with 20 kV or greater but less than 25 kV, and 1 for cases with 25 kV or greater.

For 5-grade sensory evaluation, each of the above properties was rated from the evaluation and measurement result of every Examples and Comparative Examples in a relative manner based on the following standard.

5: Good (O)
4: Fairly good (Δ-O)
3: Neutral (Δ)
2: Fairly poor (X-Δ)
1: Poor (X)

TABLE 1

| | | | | | | | | | | | |
|---|---|---|---|---|---|---|---|---|---|---|---|
| | | | colspan="9" | Hair oil | | | | | | | |
| | Ingredient | | Name | Ex. 1 | Ex. 2 | Ex. 3 | Ex. 4 | Ex. 5 | Ex. 6 | Ex. 7 | Ex. 8 | Comp Ex. 1 |
| A | | | 1. bis-diethylene glycol ethyl ether succinate | 5.00 | 10.00 | 15.00 | 20.00 | 40.00 | 45.00 | — | 50.00 | — |
| | | | 2. bis-tripropylene glycol isopropyl ether succinate | — | — | — | — | — | — | 10.00 | — | — |
| B | Volatile oil | | 3. isododecane | 45.00 | 35.00 | — | 20.00 | 30.00 | 25.00 | 65.00 | 18.95 | 45.00 |
| | | | 4. isohexadecane | — | 5.00 | 40.00 | 30.00 | — | — | — | — | — |
| | Ester oil | | 5. (polyglyceryl-2 isostearate/dimer dilinoleate) copolymer | 0.50 | — | — | — | — | — | — | 0.21 | 0.50 |
| | | | 6. isopropyl palmitate | 3.00 | — | — | — | 15.00 | — | 3.00 | 1.27 | 3.00 |
| | | | 7. isostearylneopentanoate | — | 2.00 | — | — | — | 4.00 | — | — | — |
| | | | 8. neopentyl glycol diisononanoate | — | 10.00 | 6.50 | — | — | — | — | — | — |
| | | | 9. neopentyl glycol diethylhexoate | 1.00 | — | — | 10.00 | — | — | 1.00 | 0.42 | 1.00 |
| | | | 10. triisostearin | — | — | 5.00 | — | — | 5.00 | — | — | — |
| | | | 11. polyglyceryl-2 tetraisostearate | — | — | 1.00 | — | — | — | — | — | — |
| | | | 12. sodium isostearoyl lactate | — | — | 0.05 | — | — | — | — | — | — |
| | Hydrocarbon oil | | 13. mineral oil | 10.00 | — | 20.45 | — | — | — | 3.00 | 12.63 | 10.00 |
| | | | 14. squalane | — | 5.00 | 2.00 | — | 2.00 | — | — | — | — |
| | Animal/plant oil | | 15. camellia oil | 1.00 | — | 3.00 | — | — | 1.00 | 1.00 | 0.42 | 1.00 |
| | | | 16. rice bran oil | — | 1.00 | — | 1.50 | — | 1.00 | — | — | — |
| | | | 17. jojoba oil | 2.00 | — | — | 1.00 | 3.00 | — | 2.00 | 0.84 | 2.00 |
| | | | 18. shea butter | — | — | — | — | — | 0.50 | — | — | — |
| | Silicone oil | | 19. cyclomethicone | 10.00 | — | — | 5.00 | — | 14.50 | — | 4.21 | 10.00 |
| | | | 20. phenyl polysiloxane | — | 18.80 | — | 1.00 | 10.00 | — | — | — | — |
| | | | 21. dimethicone (10 mPa*s) | 2.50 | 4.00 | — | 1.00 | — | — | — | 1.05 | 2.50 |
| Others | | | 22. ethanol | 20.00 | 5.00 | — | — | — | 1.00 | 15.0 | 10.00 | 20.00 |
| | | | 23. dimethyl PABA amidopropyl laurdimonium tosylic acid | — | — | — | 0.50 | — | — | — | — | — |
| | | | 24. propylene glycol | — | 3.00 | 5.00 | 10.00 | — | — | — | — | — |
| | | | 25. dipropylene glycol | — | — | 2.00 | — | — | 2.00 | — | — | — |
| | | | 26. di(phytosteryl/octyldodecyl) lauroyl glutamate | — | 1.00 | — | — | — | — | — | — | — |
| | | | 27. green tea extract | — | 0.20 | — | — | — | — | — | — | — |
| | | | 28. benzyl oxyethanol | — | — | — | — | — | 1.00 | — | — | — |

TABLE 1-continued

| | | | | | Hair oil | | | | | |
|---|---|---|---|---|---|---|---|---|---|---|
| Ingredient | Name | Ex. 1 | Ex. 2 | Ex. 3 | Ex. 4 | Ex. 5 | Ex. 6 | Ex. 7 | Ex. 8 | Comp Ex. 1 |
| | 29. benzyl alcohol | — | — | — | — | — | — | — | — | 5.00 |
| | 30. fragrance | *Aa | *Aa | *Aa | *Aa | *Aa | *Aa | *Aa | *Aa | *Aa |
| | 31. antioxidant agent | *Aa | *Aa | *Aa | *Aa | *Aa | *Aa | *Aa | *Aa | *Aa |
| | 32. antiseptic agent | *Aa | *Aa | *Aa | *Aa | *Aa | *Aa | *Aa | *Aa | *Aa |
| Total weight (mass %) | | 100.00 | 100.00 | 100.00 | 100.00 | 100.00 | 100.00 | 100.00 | 100.00 | 100.00 |
| Evaluation results | Easy application | 5 | 5 | 5 | 5 | 5 | 5 | 5 | 4 | 3 |
| | Non-stickiness | 5 | 5 | 5 | 5 | 5 | 5 | 5 | 4 | 5 |
| | Light finish/smoothness | 5 | 5 | 5 | 5 | 5 | 5 | 5 | 4 | 3 |
| | Easiness in taking shape | 5 | 5 | 5 | 5 | 5 | 5 | 5 | 5 | 2 |
| | Hair strength | 5 | 5 | 5 | 5 | 5 | 5 | 5 | 4 | 5 |
| | Natural shine | 5 | 5 | 5 | 5 | 5 | 5 | 5 | 4 | 4 |
| | Storage stability | 5 | 5 | 5 | 5 | 5 | 5 | 5 | 5 | 5 |
| | Improvement effect on cuticle | 5 | 5 | 5 | 5 | 5 | 5 | 5 | 5 | 1 |
| | Antistatic effect | 5 | 5 | 5 | 5 | 5 | 5 | 5 | 5 | 5 |

*Aa: Adequate amount

As shown in Table 1, the hair oils comprising the oil-based hair cosmetic material of the invention of Examples 1-8 have excellent sensation upon use such as easy application, non-stickiness, light finish/smoothness, easiness in taking shape, hair strength and natural shine, as well as superior improvement effects on cuticle with excellent storage stability and antistatic effect.

Compared to this, the hair oil of Comparative example 1 comprising benzyl alcohol in place of the dibasic acid ester compound of the invention is inferior in terms of sensation upon use such as easy application, light finish/smoothness and easiness in taking shape, as well as improvement effects on cuticle compared to those of Examples 1-8, and is particularly inferior in terms of improvement effects on cuticle, light finish/smoothness, and easiness in taking shape.

Examples 9-13

(Preparation and Evaluation of Hair Gel)

Hair gels of Examples 9-13 and Comparative example 2 with the composition shown in Table 2 were prepared in accordance with the preparation method below. Properties of the hair gels of Examples 9-13 and Comparative example 2 were evaluated in accordance with the evaluation method below. Results are shown in Table 2.

(Preparation Method)

Predetermined amounts of ingredients of each composition shown in Table 2 were mixed, and they were stirred at approximately 80-105° C. for dissolution to give a homogeneous mixture. This mixture was cooled to approximately 30° C., and the hair gels of Examples 9-13 and Comparative example 2 were obtained.

(Evaluation Method)

Properties of hair gels of Examples 9-13 and Comparative example 2 were evaluated using the same method as that in the above Examples 1-8.

TABLE 2

| | | | Hair gel | | | | | |
|---|---|---|---|---|---|---|---|---|
| | Ingredient | | Name | Ex. 9 | Ex. 10 | Ex. 11 | Ex. 12 | Ex. 13 | Comp. ex. 2 |
| A | | 1. | bis-diethylene glycol ethyl ether succinate | 5.00 | 5.50 | — | 20.00 | 50.00 | — |
| | | 2. | bis-triethylene glycol ethyl ether malate | — | 2.50 | 10.00 | — | — | — |
| B | Volatile oil | 3. | isododecane | — | — | — | — | — | — |
| | | 4. | isohexadecane | — | — | — | — | — | — |
| | Ester oil | 5. | (polyglyceryl-2 isostearate/dimer dilinoleate) copolymer | — | 0.50 | — | — | — | — |
| | | 6. | dipentaerythrityl hexa(hydroxystearate/stearate/rosinate) | — | — | 1.00 | — | — | — |

TABLE 2-continued

Hair gel

| Ingredient | Name | Ex. 9 | Ex. 10 | Ex. 11 | Ex. 12 | Ex. 13 | Comp. ex. 2 |
|---|---|---|---|---|---|---|---|
| | 7. octyldodecyl neopentanoate | 8.00 | 10.00 | — | — | 3.37 | 8.00 |
| | 8. neopentyl glycol diisononanoate | 30.00 | — | 20.00 | 15.00 | 12.64 | 30.00 |
| | 9. triisostearin | — | 14.90 | — | 10.00 | — | — |
| | 10. polygryceryl-2 isostearate | 2.70 | — | 5.00 | — | 1.14 | 2.70 |
| Hydrocarbon oil | 11. hydrogenated polyisobutene | — | 5.00 | — | 2.00 | — | — |
| | 12. mineral oil | — | 50.00 | 40.00 | 35.00 | — | — |
| | 13. squalane | — | — | 2.00 | — | — | — |
| Animal/plant oil | 14. camellia oil | 1.00 | 1.00 | 1.00 | 3.00 | 0.42 | 1.00 |
| | 15. macadamia nut oil | — | 1.00 | — | — | — | — |
| | 16. jojoba oil | — | — | 2.00 | — | — | — |
| Silicone oil | 17. cyclomethicone | 40.00 | — | 5.00 | 10.00 | 16.84 | 40.00 |
| | 18. phenyl polysiloxane | — | — | 10.00 | — | — | — |
| | 19. dimethicone (10 mPa · s) | 2.00 | — | 1.00 | 2.00 | 0.84 | 2.00 |
| Others | 20. dibutyl lauroyl glutamide | 2.00 | 1.00 | — | — | 0.84 | 2.00 |
| | 21. di(C20-40)alkyl dimer dilinoleate | — | 1.00 | — | — | — | — |
| | 22. polyamide resin with amide terminal groups | — | — | 1.00 | — | — | — |
| | 23. polyamide resin with ester terminal groups | — | — | — | 1.00 | — | — |
| | 24. microcrystalline wax | 0.20 | — | — | — | 0.08 | 0.20 |
| | 25. (vinyl pyrrolidone/hexadecene) copolymer | — | — | 1.00 | — | — | — |
| | 26. (eicosene/vinyl pyrrolidone) copolymer | — | — | — | 1.00 | — | — |
| | 27. ethanol | — | — | — | — | 10.0 | — |
| | 28. octyl dodecanol | 8.00 | 2.00 | — | — | 3.37 | 8.00 |
| | 29. cetanol | — | 4.50 | — | — | — | — |
| | 30. oleth-2 | — | 0.50 | — | 1.00 | — | — |
| | 31. PEG-10 hydrogenated castor oil | 1.00 | 0.50 | — | — | 0.42 | 1.00 |
| | 32. benzyl oxyethanol | — | — | 1.00 | — | — | — |
| | 33. malic acid | 0.10 | — | — | — | 0.04 | 0.10 |
| | 34. glycolic acid | — | 0.10 | — | — | — | — |
| | 35. diethoxy ethyl succinate | — | — | — | — | — | 5.0 |
| | 36. fragrance | *Aa | *Aa | *Aa | *Aa | *Aa | *Aa |
| | 37. antioxidant agent | *Aa | *Aa | *Aa | *Aa | *Aa | *Aa |
| | 38. antiseptic agent | *Aa | *Aa | *Aa | *Aa | *Aa | *Aa |
| Total weight (mass %) | | 100.00 | 100.00 | 100.00 | 100.00 | 100.00 | 100.00 |
| Evaluation results | Easy application | 5 | 5 | 5 | 5 | 4 | 3 |
| | Non-stickiness | 5 | 5 | 5 | 5 | 4 | 5 |
| | Light finish/smoothness | 5 | 5 | 5 | 5 | 4 | 3 |
| | Easiness in taking shape | 5 | 5 | 5 | 5 | 5 | 4 |
| | Hair strength | 5 | 5 | 5 | 5 | 4 | 3 |
| | Natural shine | 5 | 5 | 5 | 5 | 4 | 5 |
| | Storage stability | 5 | 5 | 5 | 5 | 5 | 5 |
| | Improvement effect on cuticle | 5 | 5 | 5 | 5 | 5 | 2 |
| | Antistatic effect | 5 | 5 | 5 | 5 | 5 | 3 |

*Aa: Adequate amount

As shown in Table 2, the hair gels comprising the oil-based hair cosmetic material of the invention of Examples 9-13 have excellent sensation upon use such as easy application, non-stickiness, light finish/smoothness, easiness in taking shape, hair strength and natural shine, as well as superior improvement effects on cuticle with excellent storage stability and antistatic effect.

Compared to this, the hair gel of Comparative example 2 comprising diethoxy ethyl succinate in place of the dibasic acid ester compound of the invention is inferior in terms of sensation upon use such as easy application, light finish/smoothness and hair strength, as well as improvement effects on cuticle and antistatic effect, compared to those of Examples 9-13, and is particularly inferior in terms of improvement effects on cuticle, easy application, and light finish/smoothness.

Examples 14 and 15

(Preparation and Evaluation of Hair Spray)

Hair sprays of Examples 14 and 15 and Comparative example 3 with the composition shown in Table 3 were prepared in accordance with the preparation method below. Properties of the hair sprays of Examples 14 and 15 and Comparative example 3 were evaluated in accordance with the evaluation method below. Results are shown in Table 3.

(Preparation Method)

Predetermined amounts of ingredients of each composition shown in Table 3 were mixed, and they were stirred at room temperature for dissolution to give a homogeneous mixture. This mixture was cooled to approximately 30° C., and the stock solution of the hair sprays of Examples 14 and 15 and Comparative example 3 were obtained. This stock solution and a propellant (liquefied petroleum gas) in a ratio of 4:6 were filled into an aerosol can to give the hair sprays of Examples 14 and 15 and Comparative example 3.

(Evaluation Method)

Properties of hair sprays of Examples 14 and 15 and Comparative example 3 were evaluated using the same method as that in the above Examples 1-8. Here, application to hair bundles for evaluation was carried out as follows: a hair spray was sprayed on a hair bundle placed on a scale so that 0.5 g of the hair spray was attached to the bundle, then the hair spray was homogenously applied on the hair bundle by spreading it using fingers. Storage stability was evaluated as follows: hair sprays were stored in a thermostatic chamber at 40° C. for 3 months, then a hair spray was sprayed on the bundle, and changes in external appearance of each sample after spraying were evaluated

TABLE 3

| | | | Hair spray | | |
|---|---|---|---|---|---|
| Ingredient | | Name | Example 14 | Example 15 | Comp. Example 3 |
| A | | 1. bis-diethylene glycol succinate ethyl ether | 2.00 | — | — |
| | | 2. bis-tributylene glycol malate isobutyl ether | — | 3.00 | — |
| B | Volatile oil | 3. isododecane | — | — | — |
| | | 4. isohexadecane | — | — | — |
| | Ester oil | 5. (polyglyceryl-2 isostearate/dimer dilinoleate) copolymer | — | — | — |
| | | 6. octyldodecyl neopentanoate | — | — | — |
| | | 7. neopentyl glycol diisononanoate | 2.00 | 2.00 | 2.00 |
| | | 8. triisostearin | — | — | — |
| | | 9. polygryceryl-2 isostearate | — | — | — |
| | | 10. sodium isostearoyl lactate | — | — | — |
| | Hydrocarbon oil | 11. hydrogenated polyisobutene | — | — | — |
| | | 12. squalane | — | — | — |
| | | 13. camellia oil | — | — | — |
| | Animal/plant oil | 14. rice bran oil | — | — | — |
| | | 15. jojoba oil | — | — | — |
| | Silicone oil | 16. cyclomethicone | — | 0.50 | — |
| | | 17. phenylpolysiloxane | — | 0.50 | — |
| | | 18. dimethicone (10 mPa·s) | 2.00 | 1.00 | 2.00 |
| Others | | 19. ethanol | 34.00 | 33.00 | 34.00 |
| | | 20. benzyl alcohol | — | — | 2.00 |
| | | 21. fragrance | Adequate amount | Adequate amount | Adequate amount |
| | | 22. liquefied petroleum gas | 60.00 | 60.00 | 60.00 |
| Total weight (mass %) | | | 100.00 | 100.00 | 100.00 |
| Evaluation results | | Easy application | 5 | 5 | 3 |
| | | Non-stickiness | 5 | 5 | 5 |
| | | Light finish/smoothness | 5 | 5 | 3 |
| | | Easiness in taking shape | 5 | 5 | 2 |
| | | Hair strength | 5 | 5 | 5 |
| | | Natural shine | 5 | 5 | 4 |
| | | Storage stability | 5 | 5 | 5 |
| | | Improvement effect on cuticle | 5 | 5 | 1 |
| | | Antistatic effect | 5 | 5 | 5 |

As shown in Table 3, the hair sprays comprising the oil-based hair cosmetic material of the invention of Examples 14 and 15 have excellent sensation upon use such as easy application, non-stickiness, light finish/smoothness, easiness in taking shape, hair strength and natural shine, as well as superior improvement effects on cuticle with excellent storage stability and antistatic effect.

Compared to this, the hair spray of Comparative example 3 comprising benzyl alcohol in place of the dibasic acid ester compound of the invention is inferior in terms of sensation upon use such as easy application, light finish/smoothness, and easiness in taking shape, as well as improvement effects on cuticle compared to those of Examples 14 and 15, and is particularly inferior in terms of improvement effects on cuticle and easiness in taking shape.

Example 16

(Preparation and Evaluation of Hair Stick)

Hair sticks of Example 16 and Comparative example 4 with the composition shown in Table 4 were prepared in accordance with the preparation method below. Properties of the hair sticks of Example 16 and Comparative example 4 were evaluated in accordance with the evaluation method below. Results are shown in Table 4.

(Preparation Method)

Predetermined amounts of ingredients of each composition shown in Table 4 were mixed, homogeneously diluted at 105-110° C., and defoamed. Then the resulting mixture was introduced into an appropriate container and cooled to produce hair sticks of Example 16 and Comparative example 4.

(Evaluation Method)

Properties of hair sticks of Example 16 and Comparative example 4 were evaluated using the same method as that in the above Examples 1-8. Here, application to hair bundles was carried out as follows: 0.5 g of the hair stick was rubbed on the hair bundle and it was homogeneously applied over the bundle by spreading it using fingers.

TABLE 4

| | | | Hair stick | |
| --- | --- | --- | --- | --- |
| Ingredient | | Name | Example 16 | Comparative Example 4 |
| A | | 1. bis-diethylene glycol ethyl ether succinate | 15.00 | — |
| B | Volatile oil | 2. isododecane | 5.00 | 5.00 |
| | | 3. isohexadecane | — | — |
| | Ester oil | 4. (polyglyceryl-2 isostearate/dimer dilinoleate) copolymer | 2.00 | 2.00 |
| | | 5. neopentyl glycol diisononanoate | 20.00 | 20.00 |
| | Hydrocarbon oil | 6. hydrogenated polyisobutene | 1.00 | 1.00 |
| | Animal/plant oil | 7. camellia oil | 1.00 | 1.00 |
| | | 8. rice bran oil | 2.00 | 2.00 |
| | | 9. jojoba oil | 2.00 | 2.00 |
| | Silicone oil | 10. cyclomethicone | 25.00 | 25.00 |
| | | 11. dimethyicone (10 mPa · s) | 5.00 | 5.00 |
| Others | | 12. dibutyl lauroyl glutamide | 4.00 | 4.00 |
| | | 13. stearic acid | 2.00 | 2.00 |
| | | 14. microcrystalline wax | 3.00 | 3.00 |
| | | 15. octyl dodecanol | 13.00 | 13.00 |
| | | 16. diethoxy ethyl succinate | — | 15.00 |
| | | 17. fragrance | Adequate amount | Adequate amount |
| | | 18. antioxidant agent | Adequate amount | Adequate amount |
| | | 19. antiseptic agent | Adequate amount | Adequate amount |
| | | Total weight (mass %) | 100.00 | 100.00 |
| Evaluation results | | Easy application | 5 | 3 |
| | | Non-stickiness | 5 | 5 |
| | | Light finish/smoothness | 5 | 3 |
| | | Easiness in taking shape | 5 | 4 |
| | | Hair strength | 5 | 3 |

TABLE 4-continued

| | | Hair stick | |
| --- | --- | --- | --- |
| Ingredient | Name | Example 16 | Comparative Example 4 |
| | Natural shine | 5 | 5 |
| | Storage stability | 5 | 5 |
| | Improvement effect on cuticle | 5 | 2 |
| | Antistatic effect | 5 | 3 |

As shown in Table 4, the hair spray comprising the oil-based hair cosmetic material of the invention of Example 16 has excellent sensation upon use such as easy application, non-stickiness, light finish/smoothness, easiness in taking shape, hair strength and natural shine, as well as superior improvement effects on cuticle with excellent storage stability and antistatic effect.

Compared to this, the hair spray of Comparative example 4 comprising diethoxy ethyl succinate in place of the dibasic acid ester compound of the invention is inferior in terms of sensation upon use such as easy application and light finish/smoothness, as well as improvement effects on cuticle and antistatic effect compared to those of Example 16, and is particularly inferior in terms of improvement effects on cuticle and easy application and light finish/smoothness.

INDUSTRIAL APPLICABILITY

With the oil-based hair cosmetic material of the present invention, compared to conventional hair cosmetic materials, superior improvement effects on damaged hair as well as excellent sensation upon use can be provided such as imparting strength to hair and achieving a non-sticky light finish. Accordingly, the oil-based hair cosmetic material of the invention has particularly high industrial applicability in wide fields of hair cosmetics such as hair oil, hair liquid, hair gel, hair spray, hair stick and hair mousse, and is expected to significantly contribute to the development of cosmetic and cosmetic-related industries.

The invention claimed is:

1. An oil-based hair cosmetic material comprising (A) a dibasic acid ester compound of general formula (1):

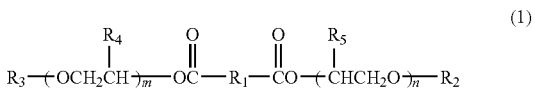

wherein $R_1$ is an alkylene group having a carbon number of 2-4, which may be mono- or poly-substituted, $R_2$ and $R_3$ are, independently of one another, an alkyl group having a carbon number of 1-4, which may be mono- or poly-substituted, $R_4$ and $R_5$ are, independently of one another, hydrogen or a methyl group or ethyl group which may be mono- or poly-substituted, m and n are both 2, and (B) one or more oil agents selected from the group consisting of a volatile oil, an ester oil, a hydrocarbon oil, an animal/plant oil, and a silicone oil, and wherein substantially no water is formulated in the hair cosmetic material.

2. The oil-based hair cosmetic material according to claim 1, wherein a poly- (or mono-)ethylene glycol monoether or a derivative thereof constituting the dibasic acid ester compound is one or more substances selected from the group consisting of diethylene glycol monoethyl ether, diethylene glycol monopropyl ether, diethylene glycol monoisopropyl ether, dipropylene glycol monoethyl ether, dipropylene glycol monopropyl ether, dipropylene glycol monoisopropyl ether, dibutylene glycol monoethyl ether, dibutylene glycol monopropyl ether, dibutylene glycol monoisopropyl ether, dibutylene glycol monobuthyl ether, and dibutylene glycol monoisobutyl ether.

3. The oil-based hair cosmetic material according to claim 1, wherein a dibasic acid constituting the dibasic acid ester compound is malic acid or succinic acid.

4. The oil-based hair cosmetic material according to claim 1, wherein the dibasic acid ester compound is bis-diethylene glycol ethyl ether succinate (bis-ethoxydiglycol succinate).

5. The oil-based hair cosmetic material according to claim 1, wherein the oil-based hair cosmetic material comprises 1.0-50% by mass of the dibasic acid ester compound based on the total mass of the oil-based hair cosmetic material.

6. The oil-based hair cosmetic material according to claim 1, wherein the oil-based hair cosmetic material comprises 0.1-99% by mass of the oil agent based on the total mass of the oil-based hair cosmetic material.

7. A hair cosmetic comprising the oil-based hair cosmetic material according to claim 1, wherein the cosmetic is non-aqueous.

8. The hair cosmetic according to claim 7, wherein the hair cosmetic is selected from the group consisting of hair oil, hair liquid, hair gel, hair spray, hair stick and hair mousse.

9. A method for preparing the oil-based hair cosmetic material or the hair cosmetic according to claim 1, comprising a step of mixing a dibasic acid ester compound with one or more oil agents.

10. A method for preparing the oil-based hair cosmetic according to claim 7, comprising a step of mixing a dibasic acid ester compound with one or more oil agents.

* * * * *